United States Patent
Kiff et al.

(10) Patent No.: US 7,652,569 B2
(45) Date of Patent: Jan. 26, 2010

(54) MOBILE TELEPHONIC DEVICE AND BASE STATION

(75) Inventors: Liana M. Kiff, Minnetonka, MN (US); Michael D. Berg, Winfield, IL (US); Scott R. Lang, Geneva, IL (US)

(73) Assignee: Honeywell International Inc., Morristown, NJ (US)

( * ) Notice: Subject to any disclaimer, the term of this patent is extended or adjusted under 35 U.S.C. 154(b) by 324 days.

(21) Appl. No.: 10/956,681

(22) Filed: Oct. 1, 2004

(65) Prior Publication Data

US 2006/0071798 A1 Apr. 6, 2006

(51) Int. Cl.
G08B 1/08 (2006.01)
(52) U.S. Cl. ............... 340/539.11; 340/539.1; 340/539.13; 340/573.1
(58) Field of Classification Search .............. 340/539.1, 340/539.11, 539.13, 573.1
See application file for complete search history.

(56) References Cited

U.S. PATENT DOCUMENTS

| | | | |
|---|---|---|---|
| 4,952,928 A | 8/1990 | Carroll et al. ........... 340/825.54 |
| 5,410,471 A | 4/1995 | Alyfuku et al. ......... 364/413.02 |
| 5,692,215 A | 11/1997 | Kutzik et al. ................ 395/838 |
| 6,002,994 A | 12/1999 | Lane et al. .................. 702/188 |
| 6,031,455 A * | 2/2000 | Grube et al. ........... 340/539.26 |
| 6,108,685 A | 8/2000 | Kutzik et al. ................ 709/200 |
| 6,246,992 B1 | 6/2001 | Brown .......................... 705/2 |
| 6,277,072 B1 | 8/2001 | Bardy ....................... 600/300 |
| 6,402,691 B1 | 6/2002 | Peddicord et al. ........... 600/300 |
| 6,616,606 B1 | 9/2003 | Petersen et al. ............. 600/300 |
| 6,749,566 B2 | 6/2004 | Russ ........................... 600/300 |
| 6,801,137 B2 | 10/2004 | Eggers .................. 340/870.09 |
| 2002/0072348 A1 | 6/2002 | Wheeler et al. ............. 455/404 |
| 2004/0036597 A1 | 2/2004 | Mays, Jr. et al. .......... 340/539.1 |
| 2004/0039521 A1 | 2/2004 | Hathiram et al. ............. 701/207 |
| 2004/0122486 A1 | 6/2004 | Stahmann et al. ............. 607/60 |
| 2004/0146149 A1 | 7/2004 | Rogers et al. .......... 379/106.02 |
| 2004/0147817 A1 | 7/2004 | Dewing et al. .............. 600/300 |
| 2004/0147818 A1 | 7/2004 | Levy et al. .................. 600/300 |
| 2004/0147981 A1 | 7/2004 | Bardy ......................... 607/60 |

(Continued)

OTHER PUBLICATIONS

Joann Kohlbrand & Julie Foster, Human ID Implant to be Unveiled Soon, 'Wearers' of Digital Angel Monitored by GPS, Internet; available at http://wnd.com/news/article.asp?ARTICLE_ID=17601, published Aug. 13, 2000.

(Continued)

Primary Examiner—Daryl Pope
(74) Attorney, Agent, or Firm—Husch Blackwell Sanders Welsh & Katz

(57) ABSTRACT

A monitoring system for purposes of enhancing independent living incorporates a wearable communication device, such as a cellular telephone, in combination with a recharging base which might be coupled to a wire line telephone system. Either or both of the base station and wearable device can be in communication with sensors scattered through an individual's residence for purposes of collecting data pertaining to activities of daily living. Either or both of the wearable unit and base station could incorporate sensors responsive to physiological parameters of the resident. Both units can independently communicate with third party monitors to communicate data about, or direct immediate attention to the state of an individual using the system.

30 Claims, 3 Drawing Sheets

U.S. PATENT DOCUMENTS

| | | | |
|---|---|---|---|
| 2004/0153289 A1 | 8/2004 | Casey et al. | 702/188 |
| 2004/0162035 A1 | 8/2004 | Petersen et al. | 455/90.1 |
| 2004/0178913 A1 | 9/2004 | Penuela et al. | 340/573.1 |
| 2004/0199056 A1 | 10/2004 | Husemann et al. | 600/300 |
| 2004/0199221 A1 | 10/2004 | Fabian et al. | 607/60 |
| 2004/0199409 A1 | 10/2004 | Brown | 705/3 |
| 2004/0203961 A1 | 10/2004 | Rustici et al. | 455/466 |
| 2004/0260463 A1 | 12/2004 | Hathiram et al. | 701/207 |

OTHER PUBLICATIONS

PCT International Search Report; Jul. 31, 2006; Int'l App. No. PCT/US05/23298; 3 pages.

PCT Writen Opinion of the International Searching Authority; Jul. 31, 2006; Int'l App. No. PCT/US05/23298; 5 pages.

* cited by examiner

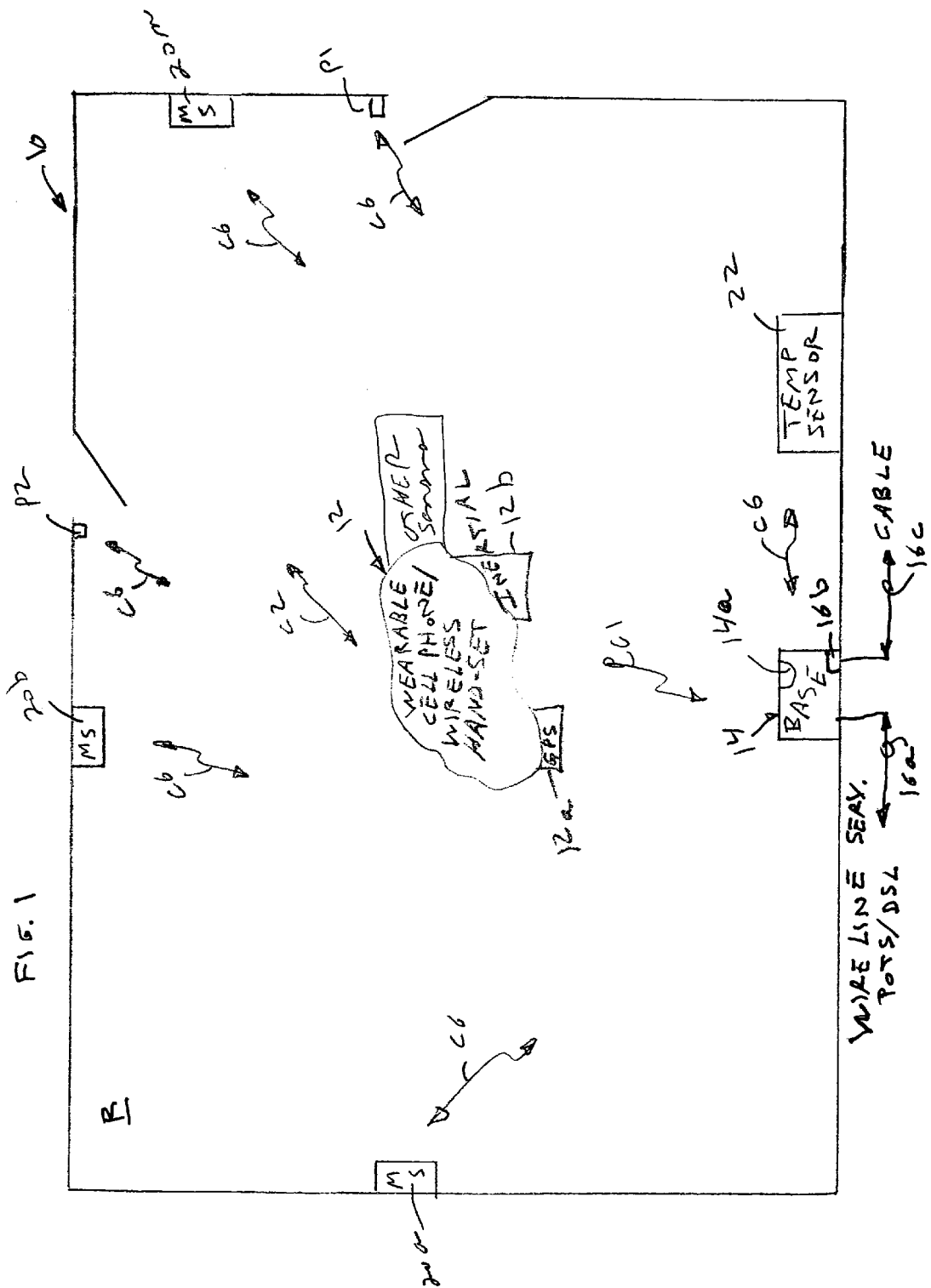

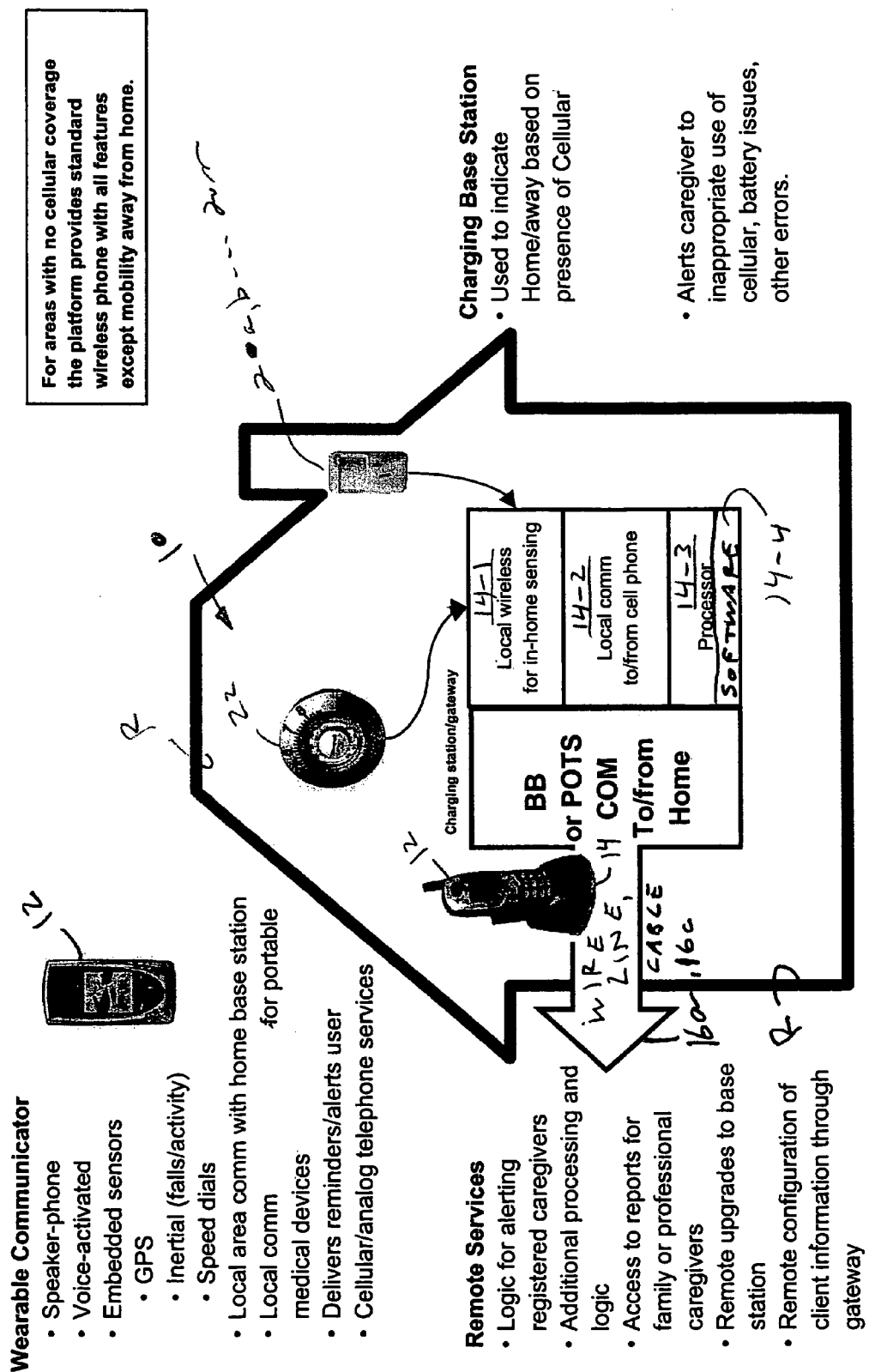

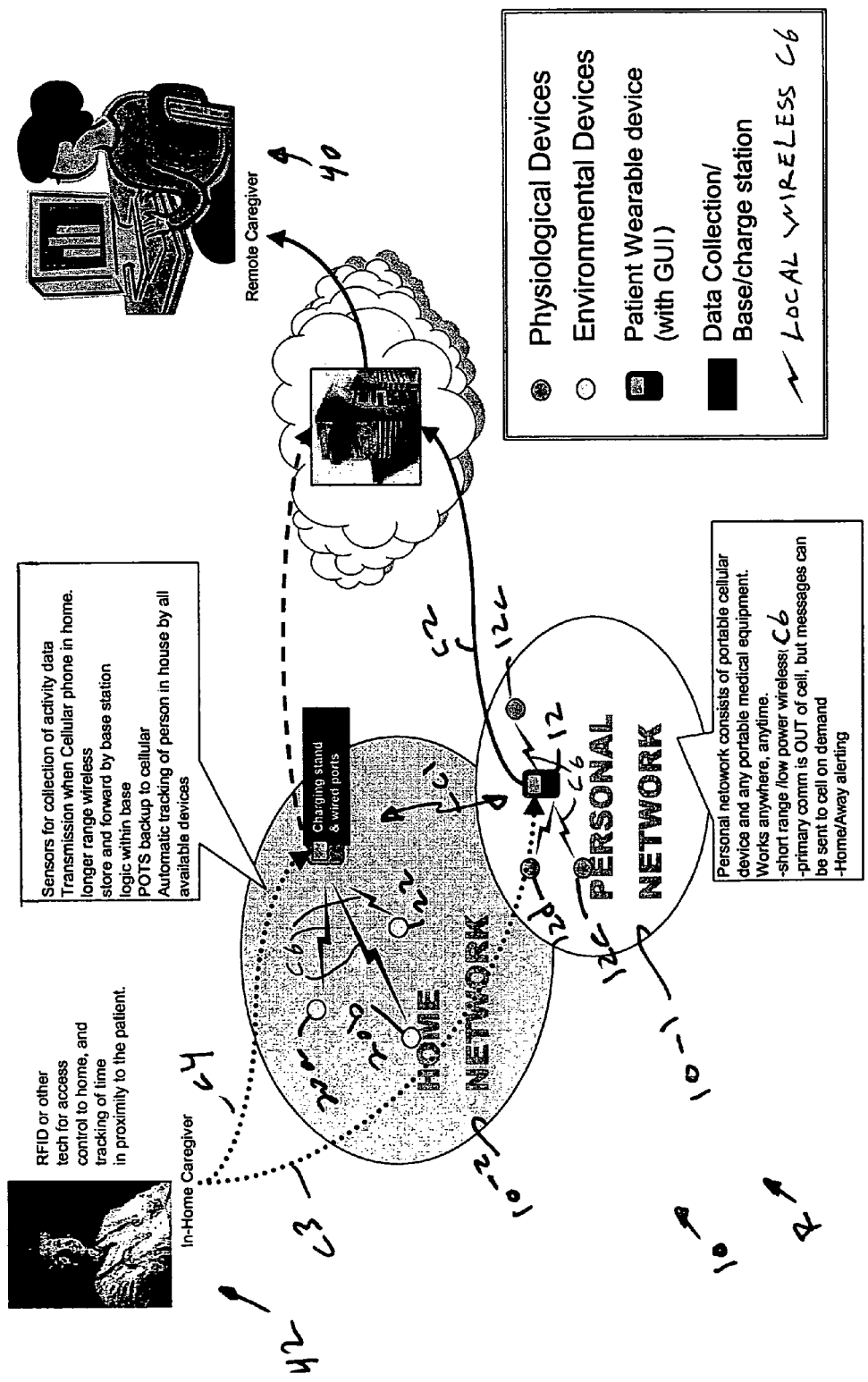

MOBILE TELEPHONIC DEVICE AND BASE STATION

FIELD OF THE INVENTION

The invention pertains to systems and methods which can support independent living of individuals who may need assistance. More particularly, the invention pertains to systems and methods which can assess and monitor activities of daily living, and physiological indicators of the health of such individuals, and facilitate appropriate communication to assist them in continuing to live independently.

BACKGROUND OF THE INVENTION

The ability to live independently hopefully evolves as a person matures through early adulthood and then extends through most or all of that person's life. However, such is not always the case.

It has been recognized that as individuals age, they lose a portion of their ability to independently carry out the activities of daily living. Common types of problems include loss of coordination and/or ability to understand where one's body is in space. These types of deficiencies can cause individuals to lose their balance and fall. The results of such falls, such as broken hips, can incapacitate the respective individual and leave them unable to summon help. The resulting delay in response, sometimes a day or more, can result in permanent disability or death in situations where quicker response could achieve full recovery.

Other forms of deficiencies arise from onset of dementia, and/or Alzheimer's Disease. Individuals with these syndromes lose their cognitive abilities, including their short term memory, in varying degrees. As a result of these losses, they often are unable to remember where they are or how to return, for example, to their residence, if they wander off (sometimes referred to as elopement). In early stages of dementia, they may simply need reminding about when to take medication, when to eat, and when to sleep, for example.

Younger individuals who are debilitated due to accidents (motorcycle riding, sports or the like) or diseases, such as cancer, alcoholism or hormonal imbalances represent another group whose ability to live independently may have been permanently compromised. Such individuals may also benefit from monitoring, reminders and the like.

Notwithstanding the types of deficiencies noted above, it has also been recognized that there is a substantial and important quality of life value in being able to continue to live substantially independently in one's residence. Not only is this psychologically, and perhaps physically, better for the individual (assuming the lifestyle can be carried out safely), it is substantially less expensive than maintaining the same individual in either an assisted living environment or a nursing home. Hence, there continues to be a need for systems and methods which support individuals who would like to remain at home, despite the presence of physical or cognitive limitations (which might have been caused by aging, accident or disease). Preferably, such systems would enable such individuals to safely remain in their homes and assist them in continuing to be as independent as possible.

BRIEF DESCRIPTION OF THE DRAWINGS

FIG. 1 is a top plan view of a portion of a residence which incorporates a system in accordance with the invention;

FIG. 2 is a schematic diagram of a side elevational view of the residence illustrating additional details of the system of FIG. 1;

FIG. 3 is an overall block diagram of a system as in FIG. 1 used to implement a care giving and monitoring methodology in accordance with the invention.

DETAILED DESCRIPTION OF THE EMBODIMENTS

While embodiments of this invention can take many different forms, specific embodiments thereof are shown in the drawings and will be described herein in detail with the understanding that the present disclosure is to be considered as an exemplification of the principles of the invention and is not intended to limit the invention to the specific embodiment illustrated.

In accordance with one embodiment of the invention, a portable telephone device, which might be wearable for example, can incorporate one or more sensors, such as fall indicating or activity sensors in combination with position indicating circuitry useable for example with a global positioning system. Other sensors and devices within the individual's home or living area can be used to monitor activities of daily living. These include, for example, one or more environmental temperature sensors, such as thermostats or motion sensors to keep track of movement of the individual within an area. In addition to the aforementioned passive monitoring devices that do not require conscious interaction by the monitored individual the system may include manual devices, such as a panic button, or speed dial facility, that puts an individual in immediate contact with a responder during a personal emergency. Additionally, position sensors, such as switches, can be associated with doors or windows to provide feedback signals indicative of the opening and closing thereof. These can be used to indicate that the respective individual may have departed from the immediate area.

In a disclosed system and method, the system and other people using the system can communicate directly with the individual being monitored. Further, the monitored individual can communicate using a wearable device.

In one embodiment of the invention, a wearable communicator, which might be a cellular telephone or a wireless hand set for a wired telephone can provide the individual with immediate access to assistance. Speed dialing capability can be provided as well as voice activation. The unit can be configured to operate in a hands free mode. Prompts or other types of alerts can be delivered to the communication device, which can be used to provide medication reminders or the like. Further, such devices can automatically detect situations such as a fall or a cessation of movement. Either of these circumstances are potentially indicative of critical situations.

The communications device can wirelessly communicate with a local base or charging station. The base or charging station can also receive data or signals from other sensors or equipment which has been installed in the residence or region being monitored. The base or charging station can provide backup communications, via a wired, or, land line telephone system in the event that the communication device fails, or, the cellular system is temporarily disrupted or unavailable.

The communication device can be slid into a docking port on the base to recharge it. The base station can respond to wired or wireless signals from one or more environmental sensing devices (e.g., temperature sensor), one or more activity sensing devices (e.g., motion sensors, contact switches) as well as one or more position sensing devices (e.g., RFID). This information can be transmitted wirelessly to the wearable communication device, or, can be transmitted via the land line connection to an external third party monitor.

The base station can also forward information to the third party monitor as to any problems detected with use or operation of the wearable communication device, battery charging problems or other sensed conditions which indicate deviations from normal activities of daily living. The base station can also, via regular monitoring of the wearable communication device determine that the device is or is not still within local range. The departure of the wearable communication device from the local region might be indicative of an elopement problem.

The local base station can also implement supervisory algorithms to prompt the user to put the device on in the morning, or put it back in the cradle at night, thus ensuring both proper re-charging, and encouraging and reminding them to wear and use the device.

In another embodiment of the invention, the wearable communication device can be in communication with wearable physiological condition measurement devices such as blood pressure sensors, blood sugar sensors, individual temperature, pedometers and the like all without limitation.

In instances where the wearable device contains embedded activity sensors (e.g., fall sensor, pedometer) the device may be designed to be worn on or near the torso, for example, on the person's belt, or upper arm, where these sensing activities are most accurately achieved. In other embodiments without these sensing requirements, the wearable communicating device may be designed to be worn on the extremities (e.g., wristwatch) or as an item of jewelry (e.g., pendant).

FIG. 1 illustrates an exemplary system 10 which embodies the invention. The system 10 incorporates a wearable or portable communication device 12 and an associated charging or base station 14. The wearable communication device 12 could be implemented as a cellular telephone, or as a wireless handset for a wire line phone.

The device 12 can incorporate circuitry for use with positioning systems (e.g., global positioning system, magnetometers or cellular triangulation) to identify the location thereof, or inertial sensors (e.g., accelerometers, gyroscopes, motion sensors) to provide indicia of activities of the individual carrying or wearing the device 12 (e.g., general motion, or specific occurrences such as falling). Other types of sensors which can be incorporated include temperature sensors, pedometers, or blood pressure monitors, all without limitation.

The charging or base station 14 can include a docking port indicated generally at 14a for receipt of the portion of the device 12 for storage and recharging any batteries in the device 12. The base 14 can be adapted to be coupled one or both of a wire line telephone system for purposes of providing telephone service to the base 14, or broad band, DSL type services. Alternately, the base 14 could be coupled to a cable modem 16b and a broadband cable system 16c for communications purposes.

The portable wearable device 12 can be in local bi-directional wireless communication C1 with the base 14 using any one of a variety of available protocols as would be understood by those of skill in the art. Where the device 12 is a cellular telephone, it can carry out communications via channel C2 independent of the base 14.

If the device 12 is a wireless hand set, the wireless communications could in one embodiment, be with base 14, which in turn is coupled to system 16a. Alternately, the device 12 could be in wireless communication with a standard telephone base station which would in turn be coupled to a wire line telephone system such as 16a.

As illustrated in FIG. 1, base 14 has been installed in a residence or residential region R. Region R might be some or all of a residence of an individual who could be carrying or wearing the device 12. It will be understood that while FIG. 1 illustrates a portion of such a residence, the configuration and size of the region R are not limitations of the present invention.

The system 10 can also incorporate motion sensors, such as sensors 20a, 20b . . . 20n which are dispersed about the region R. The motion sensors 20a, 20b . . . 20n can be in wireless communication with the base station 14. Alternately, they can be in wireless communication with the portable device 12.

Signals from the sensors 20a, 20b . . . 20n could be used to monitor daily living activities of the respective individual in the region R. These could include being able to ascertain if the individual is moving about the region R in a normal fashion without appearing to be experiencing any motion related emergencies. Alternately, the sensors 20a, b . . . n could provide signals to either the wearable unit 12 or base station 14 indicative of a cessation of motion which might be indicative of an abnormal condition. In such event, either the wearable unit 12 or base station 14 could communicate the lack of motion to a third party monitor for purposes of follow-up and investigation.

In addition, a thermostat or regional temperature sensor 22 can be provided in the region R and coupled to the base 14 and/or the wearable unit 12 for purposes of monitoring the temperature in the residence. Other medical devices such as oxygen supplies, or, self-standing physiological monitors, not carried by unit 12, could also be present in region or residence R and communicate wirelessly or be wired (continually or intermittently) to either the base station or the wearable communicator.

FIG. 2 illustrates additional details of the characteristics of the system 10. The remote services which can be provided via the communication link 16a can include capabilities for additionally processing signals received by the base 14 for purposes of alerting caregivers and the like to situations or trends. Information such as medication reminders can also be fed to base 14 and then to wearable unit 12 via the wireless communication link therebetween to provide various types of reminder information to the wearer of the device 12.

Other types of communications, without limitation, include being able to provide remote upgrades to the base station 14 or the wearable device 12, providing client information to the base station 14, providing feedback to the client from remote caregivers via device 12 or 14. Signals and information provided by the system 10 can be coupled via a base 14 to be integrated with external data associated with the respective resident or wearer of the communication device 12.

Base unit 14 can include a local sensor wireless interface 14-1 and communications circuit 14-2 to implement link C1 for communicating with unit 12. A processor 14-3 and associated software 14-4 can control the operation of base 14.

The base station 14 can also provide additional capability such as having a port for an additional battery for the device 12, which can be kept fully charged. Uploading collected sensor data to the wearable device 12 either via the wireless link or when the wearable device 12 is installed in docking port 14a.

The base 14 can also carry a display to enhance communication with the resident. Finally, the wearable unit 12 and the base station 14 each have the capacity to independently place outgoing communications or calls in the event that an emergency has been detected in the region R.

FIG. 3 illustrates the system 10 as it might be configured for use with a third party remote caregiver 40. In such an instance, an in-home caregiver 42 might also be available.

The caregiver 42 could carry, for example, a radio frequency identification tag (either passive or active) to provide access to the region R as well as to provide tracking of time and services, when rendered as well as the duration thereof.

As illustrated in FIG. 3, system 10 includes a personal network 10-1 implemented by unit 12 with on-board sensors, such as 12a, b. The unit 12 can be in wireless communication with additional physiological devices or sensors 12, c, d and 12e, which may be portable. The unit 12, and network 10-1 can be within, adjacent to or displaced from home network 10-2.

Home network 10-2 includes base 14 as well as sensors 20a, 20b . . . 20n and 22 (in residence of region R). Activated RFID tag(s) carried by care giver 42 can communicate, links C3, C4, with either or both of units 12, 14.

The present system and method could be used in a single person living environment. Alternately, it could be used in a multi-person community environment in conjunction with numerous different peripheral devices usable by multiple persons.

It will also be understood that the present system is modular with various sensors or other units usable with either the portable communications device or the base without limitation. The sensors or other units are preferably interchangeable and can be automatically identified by the respective device or base.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed:

1. A system comprising:
    at least one portable, wireless communications device;
    a base station for receiving and recharging the device, the base station is adapted to engage in wired communication with a communications network;
    a supervisory algorithm disposed within the base station that prompts a person to wear the portable communication device in the morning and place the portable communication device in the base station at night; and
    a plurality of physiologic sensors disposed within a residence of the person and directly responsive to the presence of the person within the residence, the sensors monitor the daily living activities of the person and wherein at least some of the plurality of physiologic sensors are coupled to the device and wherein the plurality of sensors includes at least one position indicating sensor coupled at least to the base station, the position indicating sensor is displaced from the base station.

2. A system as in claim 1 where at least some of the sensors report movement of persons in the vicinity of the sensors.

3. A system as in claim 1 where the device comprises at least one of a cellular wireless phone, or, a wireless hand-set of a wire line telephone.

4. A system as in claim 1 where the base station includes at least one port for coupling to at least one of a temperature sensor, a blood pressure sensor, a glucose sensor, or, a scale.

5. A system as in claim 4 where the temperature sensor responds to an environmental temperature.

6. A system as in claim 1 where the portable device includes at least one of circuitry for communicating with a location sensing system, or, fall detection circuitry.

7. A system as in claim 1 where the base station monitors sensor signals indicative of movements of the person in the vicinity thereof.

8. A system as in claim 7 where the base station includes software that analyzes sensor outputs to infer information about the activities of a person.

9. A system as in claim 8 where the base station includes software that communicates analysis results to at least one of another person or system via the communications network.

10. A system as in claim 1 where the communications device comprises at least one of location sensing circuitry, or, activity sensing circuitry.

11. A system as in claim 1 where the base station stores data for upload over a land-line telephone system.

12. A system as in claim 11 where the base station implements protocols indicating the urgency of data to be communicated.

13. A system as in claim 12 where the base station can take control of the land-line communication channel and deliver selected information immediately.

14. A system as in claim 1 where the base station is in substantially constant communication with other systems or persons via a substantially continuously available computer network.

15. A system as in claim 1 where the base station processes and communicates messages relative to at least one of equipment status or a person.

16. A system as in claim 3 that includes circuitry which detects whether the device is in use.

17. A system as in claim 15 which includes circuitry integral to the device that indicates that the device is in a predetermined wearing position.

18. A system as in claim 15 which includes circuitry integral to the device that can infer and report the state of the device as being worn, or not worn, through an analysis of signals from embedded sensors.

19. A system as in claim 1 which includes a portable charging unit for remote charging of the portable device when not co-located with the base station.

20. A monitoring system comprising: first and second units, one unit includes a portable, wireless, voice activated communications device for communicating via a first channel, the other unit includes circuitry for communicating with third parties via a wired network, the two units are in wireless communication with each other via a second channel; the other unit implementing a supervisory algorithm that prompts a person to wear the portable communication device in the morning and place the portable communication device in a cradle of the other unit for recharging at night; and a plurality of physiological sensors disposed within a residence of a person and directly responsive to the presence of the person within the residence, the sensors monitor the daily living activities of the person and at least some of which are coupled to each of the first and second units.

21. A system as in claim 20 where data from the sensors is wirelessly communicated to the second unit.

22. A system as in claim 20 where the at least one sensor comprises at least one of a movement indicator, a body temperature sensor, a blood pressure sensor, or a glucose sensor.

23. A system as in claim 22 where information from the at least one sensor is wirelessly communicated via at least one of the first channel, or the second channel.

24. A system as in claim 23 where the communication is indicative of a potential emergency condition and is automatically communicated to a third party.

25. A system as in claim 24 where the first unit includes circuitry for identifying the unit's location.

26. A system as in claim 25 where the first unit circuitry communicates wirelessly with elements of a global positioning system.

27. A system as in claim 20 where the communications device of the first unit includes a cellular telephone.

28. A system as in claim 27 where the telephone includes hands-free circuitry.

29. A system as in claim 28 where the telephone includes automatic dialing circuitry.

30. A system as in anyone of claims 1 and 20, where logic for data analysis and reporting may be located in one or both of the wireless communicating device or the base station.

* * * * *

UNITED STATES PATENT AND TRADEMARK OFFICE
CERTIFICATE OF CORRECTION

| | | |
|---|---|---|
| PATENT NO. | : 7,652,569 B2 | Page 1 of 1 |
| APPLICATION NO. | : 10/956681 | |
| DATED | : January 26, 2010 | |
| INVENTOR(S) | : Kiff et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 597 days.

Signed and Sealed this

Twenty-third Day of November, 2010

David J. Kappos
*Director of the United States Patent and Trademark Office*